United States Patent [19]

Baldwin et al.

[11] Patent Number: 5,043,157
[45] Date of Patent: Aug. 27, 1991

[54] FELINE INFECTIOUS PERITONITIS VACCINE AND METHOD OF PREPARATION

[75] Inventors: Charles A. Baldwin, Stillwater, Okla.; Fredric W. Scott, Brooktondale, N.Y.

[73] Assignee: Cornell Research Foundation, Inc., Ithaca, N.Y.

[21] Appl. No.: 163,059

[22] Filed: Mar. 2, 1988

Related U.S. Application Data

[63] Continuation-in-part of Ser. No. 826,638, Feb. 6, 1986, abandoned.

[51] Int. Cl.$^5$ .......................... A61K 39/12; C12N 7/08
[52] U.S. Cl. ........................................ 424/89; 435/237
[58] Field of Search ........................... 435/237; 424/89

[56] References Cited

U.S. PATENT DOCUMENTS 4,021,302  5/1977  Smith et al. .
4,195,130  3/1980  Hosino et al. .
4,571,386  2/1986  Fishman et al. .................... 435/235

FOREIGN PATENT DOCUMENTS 0011864  6/1980  European Pat. Off. .
0027347  4/1981  European Pat. Off. .

OTHER PUBLICATIONS

Scott, "Immunization Against Feline Infectious Peritonitis" 1988 Eastern States Veterinary Conference; Orlando, Fla.
Barlough, Vet. Clin. North Am. Small Anim. Pract. 14:955-969 (1984).
Barlough, J. Small Animal Pract., 26:353-362 (1985).
Scott, Proceedings of the 2nd Annual Kai Kan Seminar Eastern States Veterinary Conference, (1986) pp. 27-32.
Barlough et al., Can. J. Comp. Med., 49:303-307, (1985).
Barlough et al., "Feling Infectious Peritonitis", in Manual of Small Animal Infectious Diseases, Barlough (ed.) Churchill Livingston, NY pp. 63-78, (1987).
Barlough et al., "Feline Infectious Peritonitis" in Contemporary Issues in Small Animal Practice, Scott (ed.) 3:93-108, Churchill Livingston NY, (1986).
Barlough et al., Laboratory Animal Science, Dec. 1984, pp. 616-618.
Scott, "Feline Infectious Peritonitis and Other Feline Coronaviruses" in Kirk (ed.): Current Veterinary Therapy IX pp. 1059-1062. W. B. Saunders, Phil. (1986).
Scott, J. Am. Vet. Med. Assoc., 175:1164-1168 (1979).
Stoddart et al., Arch. Virol., 79:85-94 (1984).
Weiss et al., Am. J. Vet. Res., 42:382-390 (1981).
Weiss et al., Am. J. Vet. Res., 42:2036-2048 (1981).
Weiss et al., Feline Practice, 10:16-22 (1980).
Pederson, "Feline Infectious Peritonitis Virus" in Appel (ed.) Virus Infections of Carnivores, Elsevier Sci. Pub., NY, (1987) pp. 267-286.
Stoddart et al., Res. Vet. Sci. (In press. 1988).
Baldwin, Ph.D. Thesis "Immunization Studies Against Feline Infectious Peritonitis", Jun. 1968.
Pederson et al., Biological Abstracts, vol. 79, 1985, Abstract No. 59641.
Pedersen et al., Adv. Exp. Med. Biol., 173:365-380 (1984).
McKeirnan et al., Feline Practice, 11:16-20 (1981).
Pedersen et al., Am. J. Vet. Res., 45:2580-2585 (1984).

Primary Examiner—Sam Rosen
Attorney, Agent, or Firm—Jones, Tullar & Cooper

[57] ABSTRACT

It has now been discovered that feline infectious peritonitis virus, WSU FIPV 79-1146 can be attenuated to form a live modified vaccine against feline infectious peritonitis (FIP) which vaccine both imparts immunity and is safe, that it does not cause FIP in the feline.

23 Claims, No Drawings

FELINE INFECTIOUS PERITONITIS VACCINE AND METHOD OF PREPARATION

CROSS REFERENCE TO RELATED APPLICATION

This application is a continuation-in-part of application Ser. No. 826,638, filed Feb. 6, 1986 now abandoned.

BACKGROUND OF THE INVENTION

This invention relates to the immunization of felines against coronavirus (FIPV) induced infectious peritonitis (FIP).

Coronaviruses which have been isolated from cats can be divided into two groups: viruses which cause FIP and viruses which cause a transient subclinical to severe enteritis. The various isolates are all morphologically and antigenically related and probably represent stains of a common species of virus that infects cats, dogs and swine; (see Pedersen et al, *Adv. Exp. Med. Biol.*, 173:365-380 (1984).

The development of a vaccine against FIP has eluded investigators for some time. Pedersen et al, supra, summarize the state of the art which indicates that FIPV antibodies actually can sensitize felines to the disease. The literature has reported that following immunization with live alternated virus, challenge with virulent virus caused increased infection rates, reduced latency periods and enhanced disease severity.

FIPV 79-1146 is a virus strain originally isolated by James F. Evermann, Washington State University and has been characterized inter alia by McKeirnan et al, *Feline Practice*, 11:16-20 (1981); Pedersen et al supra and Pedersen et al *Am. J. Vet. Res.*, 45:2580-2585 (1984).

U.S. Pat. No. 4,195,130 is drawn to the propagation of FIPV virus in tissue culture and is hereby incorporated by reference.

DESCRIPTION OF THE INVENTION

It has now been discovered that feline infectious peritonitis virus, WSU FIPV 79-1146 can be attenuated to form a live modified vaccine against feline infectious peritonitis (FIP) which vaccine both imparts immunity and is safe, that it does not cause FIP in the feline.

The present invention relates to a method of protecting felines against FIP, a method of producing a non-virulent attenuated living FIPV for use as a safe, efficacious vaccine, and the resultant vaccine.

The attenuation of the virus is accomplished by serial passaging in cell culture, preferably non-oncogenic cell culture, in which virus growth occurs, at a temperature which causes virus growth and attenuation until a non-virulent immunizing virus is produced. Felines vaccinated with the attenuated strain did not suffer significant illness when challenged by a virulent strain of FIPV.

The cell culture employed in passaging the virus can be any cell culture in which the virus replicates, for example, whole fetus cells (e.g. FCWF, *Felis catus* whole fetus), feline kidney cells (e.g. CrFK, Crandell Feline Kidney), feline lung cells and A-72 (a canine tumor cell line). Preferably the cell culture is a non-oncogenic cell culture. See also U.S. Pat. No. 4,195,130, previously incorporated.

The temperature at which the virus is grown can be any temperature at which with tissue culture passage attenuation occurs. The presently preferred temperature is a sub-optimal temperature, that is a temperature lower than the normal body temperature for a feline but at which virus growth occurs. The presently preferred temperature range is between about 33° C. and about 35° C.

The number of passages required to obtain safe, immunizing attenuated virus is dependent at least in part on the conditions employed and in part on the age of the felines being vaccinated. Periodic testing of the culture for virulence and immunizing ability can readily determine the parameters for a particular combination of tissue culture and temperature.

It has been discovered that kittens appear more susceptible to FIPV than do adult felines. As an apparent consequence, an attenuated living FIPV which is sufficiently attenuated to be safe for and will immunize adult felines, may still be sufficiently virulent to cause significant disease symptoms or reactions in kittens. This was found to be the case with the 19 passage attenuated as set forth in the Examples. However, a 40 passage attenuated virus was both safe and effective in imparting immunity in both adult felines and kittens.

Typically the required number of passages in obtaining a safe useful vaccine for all felines is at least about 35 passages and preferably at least about 40 passages. Although a safe useful vaccine for adult felines (i.e. felines six months old or older) can be obtained after at least about 15 passages and preferably at least about 20 passages.

In the preferred embodiment of the invention, an attenuated live FIP vaccine is produced by serially passaging the native virulent virus WSU FIPV 79-1146 at least about forty times in CrFK at a temperature between about 33° C. and about 35° C.

The vaccine of this invention can be administered by any route which causes an increase in antibody titer in the feline. The presently preferred route is intranasal or oral administration. Subcutaneous administration is also contemplated as effective.

EXAMPLE 1

The virus used in the Examples was the strain WSU FIPV 79-1146, originally isolated by Dr. J. F. Evermann at Washington State University. It was supplied, at approximately the sixth passage level, to the Cornell Feline Health Center by Dr. Neils Pedersen from the University of California at Davis. The original isolate was made from a kitten that had died soon after birth of pneumonia and pleuritis. Direct examination of the virus by electron microscopy demonstrated two populations present morphologically. One population, constituting 95-98% of the virions seen, was the typical FIPV with short, more tear-dropped-shaped peplomers. The other population was approximately 2-5% of the virions present and had longer, more bulbous-shaped peplomers present. Since it appeared that a mixed isolate was present, the virus was plaque purified and cloned, as described below, three times prior to use in these experiments.

The $UCD_1$ strain of FIPV employed as a challenge virus was originally obtained from Dr. Neils Pedersen at the University of California, Davis. The prior history of the virus included several passages through minimal disease cats. A 50% liver suspension was made upon the death of the cats at each passage and the suspension was stored at −70° prior to its being used as a challenge virus. The $UCD_1$ virus strain is a highly virulent one and has been used as a challenge virus at the Cornell Feline Health Center for many years. It consistently produced specific lesions followed by death when the suspension was given by aerosolization to cats.

All of the WSU FIPV 79-1146 viral strains were first grown in one cell line, Felis catus whole fetus cells (FCWF's), which were supplied by Dr. Neils Pedersen. Growth media for these cells included equal volumes of Leibowitz's ($L_{15}$) (Gibco Grande Island Co., Grande Island, N.Y.) and Dulbecco's modified minimal essential media (DMEM) (GIBCO) supplemented with 10% fetal bovine serum. It was found to be necessary to include in the growth media 0.05% Lactalbumin hydrosylate (LAH) (GIBCO), 1% MEM sodium pyruvate and 1% nonessential amino acids (GIBCO). The antibiotics Fungizone and Gentamicin (GIBCO), were also added. When the cells had grown to a complete monolayer, they were split and transferred. The FCWF cells did poorly and in all later experiments Crandall feline kidney (CrFK) cells or A-72 cells were used. Media used to propagate the cells consisted of 20% $L_{15}$, 3% 0.1N NaOH, 2% L-glutamine (GIBCO). To transfer the cells, the growth media was removed and, depending on the size of the tissue culture flask, up to 7 cc of crude porcine trypsin-versine in phosphate buffered saline were added as a wash. After 30 seconds, this trypsin wash was removed and a second volume of the trypsin was added. The flask was incubated for 5-10 minutes at 37° C. After the time had elapsed and when the cells had been dispersed into single cells, new growth media was added to a volume three times the original volume, for a one to three cell split. The cells were then dispensed into the new flasks as the protocol demanded.

To grow the virus strains, the growth medium was removed from complete monolayers and the cells were washed once with MEM. This was removed and the viral inoculum was added. The flask was rocked on a Belco Low-Profile Rocker (Belco Glass, Inc., N.J.) for one hour at 37° C. at a speed of approximately 2 oscillations per minute. After one hour, new growth medium was added and the flasks were incubated at 37° C. All the culture flasks were examined daily for cytopathic effect. When approximately 60-80% of the monolayer was infected, the flasks were frozen at −70° C. After three freeze/thaw cycles, the virus supernatant was centrifuged at 2000 RPM at 4° C. in an IEC, DPR-6000 centrifuge (Damon, Needham Heights, Mass.). The supernatant was aliquoted into 1 volumes and frozen at −70°.

To plaque-pick or clone a virus, growth medium was removed from confluent monolayers in 6-well plates. The monolayer was washed once with MEM and the wash was then removed. Serial ten-fold dilutions, in MEM, of the virus, and 0.1 to 0.5 cc was inoculated into duplicate wells. The virus was allowed to adsorb for one hour at 37° C. on a Belco Rocker. After one hour, the inoculum was removed, the monolayer was washed once with MEM, and the overlay added. The overlay consisted of equal volumes of 2×BME (Gibco) and 1.8% Agarose (Seakem-ME-FMC Corp, Rockland, Me.). In addition, the antibiotics Fungizone and Gentamicin were added. The plates were examined daily for plaque production. When isolated plaques were seen, the clones were picked with the use of tuberculin syringes with 1" or 1½" 20 gauge needles, and the clone was added to a vial containing 1 cc of MEM. If not inoculated immediately into flasks, the clones were frozen at −70° C. for future use. After the plaques were picked, the plates were stained with a solution consisting of one gram crystal-violet per liter of 10% buffered formalin solution and examined to determine which was the most isolated of the plaque(s) picked. The isolated clones that had been picked were then grown up and the virus was replaqued for more clones. After the third cloning procedure, the virus was considered "pure," was grown up in large flasks, aliquoted into vials, and frozen at −70° as the stock inocula for future experiments. This stock inocula was considered to be low passage virus (LP) and was approximately at passage level 11.

After the virus had been cloned, the LP virus was passaged several more times in 480 $cm^2$ roller bottles but at 34° C. At passage level 16 a large flask wa inoculated with virus, adsorbed for one hour with continuous rolling and maintenance media added. When the amount of cytopathic effect had reached approximately 75%, the flask was frozen and thawed for three times. The virus was then stored and was designated high passage virus (HP). It was approximately passage level 17 and had only been propagated at 34° C. since the plaque purification procedure. This HP virus was also considered to be a temperature-sensitive and was used as vaccine virus.

To perform virus neutralization tests (VN), serum samples were heat inactivated for 35 minutes in a 56° C. water bath. After heat inactivation, two fold dilutions of serum were made in either MEM, $L_{15}$, or PBS. An equal volume of virus containing 100 $TCID_{50}$ was then added to each serum sample. The serum-virus mixture was then incubated for one hour at 37° C. Following incubation, 0.2 cc of the serum-virus mixture was added in triplicate wells to a 48-well Costar plate that had been just seeded with CRFK cells. For the virus control, only 0.1 cc was added to each well. The tissue culture control had 0.1 cc of the diluent added to each well. The plates were then sealed in plastic bags and incubated at 37° C. for 4 days. On the fourth day, the medium was removed and the plate immersed in a crystal violet staining tank containing 10% formalin for 10 minutes. The plates were rinsed with water, allowed to dry and the sample was titered. The end point titer wa considered to be the last dilution in which there was complete neutralization of the virus or in which there was complete protection of the cell monolayer.

To assess the cytopathic effect produced by WSU FIPV 79-1146, confluent monolayers in 24-well plates with coverslips were inoculated with ten-fold dilutions of the virus. After a one-hour adsorption period, maintenance medium was added. Thereafter, at 6-hour intervals, an infected coverslip and a tissue culture control coverslip were removed. The coverslips were washed once in PBS and then fixed for ten minutes in methanol. After fixation, the coverslips were stained for ten minutes in May—Breenwald stain (Harelco, Gebbstown, N.J.), followed by a 20 minute staining period in a 1/20 dilution of Giemsa stain. The coverslips were then washed twice in distilled water, washed twice for 15 seconds in acetone, dehydrated in acetone-xylene mixtures, and finally immersed in pure xylene for ten minutes. The coverslips were then removed, mounted on glass microscope slides for a permanent mount using Permount (Fisher Scientific, Fairlawn, N.J.) and examined.

The 11th Cornell passage of FIPV 79-1146 (total 17th passage) was used as challenge virus and for the intratracheal "1st vaccination" or virus titration (Table 1). Attenuation of virus was done by rapid passage in cell cultures at low temperature (34° C.). A total of 7 low temperature passages were done in a sequence of canine A-72 cells (3 passages), and Crandell feline kidney cells (CrFK) (4 passages). The attenuated virus (19 passage attenuated virus) used in this study had 7 low temperature (34° C.) CrFK cell culture passages and a total of 19 cell culture passages.

Fourteen (14) 6-month old specific pathogen free (SPF) cats (Liberty Lab) were placed into filter isolation cages and exposed to varying doses of low passage (12th passage) FIPV 79-1146 via intratracheal inoculation. Cats were monitored daily for signs of clinical disease and fever. Weekly serum samples were obtained for virus neutralizing (VN) antibody titer against FIPV 79-1146.

The results of the viral titration or "1st vaccination" are listed in Table 1. The minimal infectious dose was 103 plaque forming units (PFU) of virus. One of 2 cats receiving 103 PFU of virus became infected and died on day 56 after inoculation. Cat Q3 seroconverted to FIPV 79-1146 virus and developed signs of FIP including ocular and chest involvement, but this cat did not succumb until after aerosol challenge. Cat R4 developed FIP and died on day 28. Three cats that seroconverted to FIPV 79-1146 (cats N4, J1 and S2) did not show any signs of illness.

After an observation period of 134 days, the cats remaining from the previous experiment were given a "2nd vaccination" with $10^4$, $10^5$, or $10^6$ TCID$_{50}$ of attenuated WSU FIPV 79-1146 virus (19th passage) via intranasal drops. None of the cats showed any signs of illness during the observation period (49 days) after the 2nd vaccination. All vaccinated cats that were seronegative at the time of vaccination seroconverted with maximum titers of 1:64 to 1:256. There did not seem to be any correlation between the dose of virus and the resulting titer. Three of the 4 cats with FIP VN antibody titers at the time of revaccination had a 2 to 4 fold rise in titer.

Forty-nine days after the second vaccination (day 183 of the experiment), cats were challenged via aerosol with either low passage FIPV 79-1146 virus or the highly virulent liver suspension of strain UCD$_1$. The experimental design and results of this challenge experiment are listed in Table 1. The low passage 79-1146 virus was the same stock virus used in the intratracheal inoculation in the first part of this experiment. The UCD$_1$ challenge virus was the stock liver suspension of highly virulent virus used in numerous challenge trials with FIP over the last 10 years. Prior to this study, the UCD$_1$ virus has been fatal for nearly 100% of cats infected within 1 to 2 weeks in seropositive cats and within 3 to 4 weeks in seronegative cats. The one unvaccinated cat (cat V1) that received 1146 challenge virus developed illness and died on day 28 after challenge. Cat Q3 was euthanized on day 60 after challenge because it was showing chronic FIP similar to what it had shown for several weeks following the initial inoculation. One of 3 other antibody positive cats receiving 79-1146 virus and 2 of 4 antibody positive cats receiving UCD$_1$ virus showed transient clinical signs (fever, anorexia, and in one case, icterus), but none of these developed typical clinical FIP. Cat H3 (1146 challenge) had fever on days 4-6 after challenge, cat P4 (UCD$_1$ challenge) had a fever on days 11-24 and 43-47 as well as periodic anorexia. Fever was detected in cat S2 (UCD$_1$ challenge) on days 8-12, anorexia on days 8-14, and icteric serum on day 14 after challenge.

The data demonstrates that the 19 passage attenuated FIPV 79-1146 did not sensitize felines to either challenge with the UCD$_1$ virus or rechallenge with virulent 79-1146 virus. This is of considerable significance since, as set forth above, antibodies against several coronaviruses appear to sensitize felines so that a more acute disease is produced with exposure to UCD$_1$ or certain other feline coronaviruses.

Substantial neutralizing antibody titers against FIPV 79-1146 were produced following a single intranasal vaccination. The VN antibody titers are listed in Table 2.

TABLE 1

Response of cats to virulent and attenuated WSU FIPV 79-1146

| | Pre Vac. | 1st Vaccination (Low passage 1146 Intratracheal) | | | |
|---|---|---|---|---|---|
| Cat | VN Titer 1146 | Viral Dose (TCID$_{50}$) | VN Titer 1146 | FIP Signs | Death (days) |
| V1 | 0 | 0 | 0 | — | — |
| B3 | 0 | 0 | 0 | — | — |
| M2 | 0 | $10^1$ | 0 | — | — |
| H3 | 0 | $10^1$ | 0 | — | — |
| P4 | 0 | $10^2$ | 0 | — | — |
| O3 | 0 | $10^2$ | 0 | — | — |
| A3 | 0 | $10^3$ | 0 | — | — |
| D2 | 0 | $10^3$ | 1024 | — | 56 |
| Q3 | 0 | $10^4$ | 2048 | — | — |
| N4 | 0 | $10^4$ | 256 | — | — |
| J1 | 0 | $10^5$ | 512 | — | — |
| R4 | 0 | $10^5$ | 32 | — | 28 |
| P2 | 0 | 0 | 0 | — | — |
| S2 | 0 | $10^{5.6}$ | 512 | — | — |

| | Pre Vac. | 2nd Vaccination* (High passage of 1146 Intranasal) | | | | Challenge** (Aerosol) | | |
|---|---|---|---|---|---|---|---|---|
| Cat | VN Titer 1146 | Viral Dose (TCID$_{50}$) | VN Titer 1146 | FIP Signs | Death | FIP Virus | VN Titer 1146 | FIP Signs | Death (days) |
| V1 | 0 | Control | 0 | — | — | 1146 | 32 | — | 28 |
| B3 | 0 | Control | 0 | — | — | Control | 0 | — | — |
| M2 | 0 | $10^6$ | 256 | — | — | 1146 | 512 | — | — |
| H3 | 0 | $10^6$ | 64 | — | — | 1146 | 128 | — | — |

TABLE 1-continued

Response of cats to virulent and attenuated WSU FIPV 79-1146

| | | | | | | | | | |
|---|---|---|---|---|---|---|---|---|---|
| P4 | 0 | $10^5$ | 256 | — | — | UCD$_1$ | 2048 | — | — |
| O3 | 0 | $10^5$ | 128 | — | — | UCD$_1$ | 256 | — | — |
| A3 | 0 | $10^4$ | 256 | — | — | TC Control | 256 | — | — |
| D2 | 0 | X | X | X | X | X | X | X | X |
| Q3 | 0 | $10^4$ | 2048 | — | — | 1146 | 4096 | + | 60 |
| N4 | 0 | $10^4$ | 1024 | — | — | 1146 | 4096 | — | — |
| J1 | 0 | $10^4$ | 1024 | — | — | UCD$_1$ | 4096 | — | — |
| R4 | 0 | X | X | X | X | X | X | X | X |
| P2 | 0 | $10^4$ | 128 | — | — | TC Control | 256 | — | — |
| S2 | 0 | $10^4$ | 1024 | — | — | UCD$_1$ | 2048 | — | — |

Virus Strains
1146 = FIPV 79-1146
UCD$_1$ = Liver suspension of virulent virus
Titer = reciprocol of serum dilutions that protected 100% of cell culture infected with 100 TCID$_{50}$ of virus
− = Negative
\− = Positive
X = cat died
\* = day 134 of experiment
\*\* = day 183 of experiment

TABLE 2

Virus Neutralizing Antibody Titers of Serum against FIPV 79-1146 in Cats "Vaccinated" with Low or High Passage Virus.

| | FIPV-1146 Virus Neutralizing Antibody Titer (Cat No.) | | | | | | | | | |
|---|---|---|---|---|---|---|---|---|---|---|
| Days | A3 | P2 | N4 | Q3 | M2 | H3 | S2 | J1 | Q3 | P4 | V1 |
| 0 | 0 | 0 | 0 | 0 | 0 | 0 | 0 | 0 | 0 | 0 | 0 |
| 14 | 0 | 0 | 32 | 32 | 0 | 0 | 8 | 32 | 0 | 0 | 0 |
| 28 | 0 | 0 | 64 | 64 | 0 | 0 | 128 | 32 | 0 | 0 | 0 |
| 42 | 0 | 0 | 64 | 512 | 0 | 0 | 256 | 64 | 0 | 0 | 0 |
| 49 | 0 | 0 | 128 | 1024 | 0 | 0 | 512 | 128 | 0 | 0 | 0 |
| 56 | 0 | 0 | 128 | 1024 | 0 | 0 | 512 | 256 | 0 | 0 | 0 |
| 63 | 0 | 0 | 256 | 2048 | 0 | 0 | 1024 | 256 | 0 | 0 | 0 |
| 70 | 0 | 0 | 256 | 1024 | 0 | 0 | 1024 | 256 | 0 | 0 | 0 |
| 77 | 0 | 0 | 256 | 2048 | 0 | 0 | 256 | 512 | 0 | 0 | 0 |
| 129 | 0 | 0 | 256 | 2048 | 0 | 0 | 512 | 512 | 0 | 0 | 0 |
| 141 | 0 | 0 | 128 | 2048 | 0 | 0 | 128 | 512 | 0 | 0 | 0 |
| 148 | 128 | 8 | 1024 | 2048 | 32 | 32 | 512 | 1024 | 16 | 32 | 0 |
| 162 | 128 | 64 | 512 | 2048 | 64 | 32 | 1024 | 512 | 128 | 32 | 0 |
| 169 | 128 | 128 | 512 | 1024 | 128 | 64 | 512 | 512 | 128 | 64 | 0 |
| 176 | 256 | 128 | 512 | 2048 | 256 | 64 | 512 | 1024 | 256 | 128 | 0 |
| 183 | 256 | 64 | 1024 | 2048 | 256 | 128 | 1024 | 1024 | 128 | 256 | 0 |
| 193 | 256 | 128 | 1024 | 2048 | 128 | 64 | 512 | 1024 | 128 | 512 | 0 |
| 200 | 128 | 512 | 1024 | NA | NA | NA | 2048 | 2048 | 512 | 2048 | 32 |
| 207 | NA | 256 | 1024 | NA | 512 | NA | 512 | 2048 | NA | NA | NA |
| 214 | 512 | 512 | 2048 | 4096 | NA | NA | 2048 | 2048 | 256 | 1024 | NA |
| 221 | 256 | 256 | 2048 | 4096 | NA | NA | NA | 2048 | 256 | 2048 | NA |
| 228 | 512 | 512 | NA | 4096 | NA | NA | 2048 | 4096 | NA | 2048 | NA |

As FIPV 79-1146 was isolated from a neonatal kitten with kitten mortality complex (KMC), it would appear that KMC is an FIPV caused disease and that thus the vaccine of the invention is also effective against KMC, which is therefore included within the scope of this invention.

EXAMPLE 2

The work with 19th passage attenuated virus in adult cats (Example 1) was repeated and the 19th passage attenuated virus was also tested in 12 to 16 week old kittens.

Further the 79-1146 virus was carried through 50 passages (38 at low temperatures), and the effect of the 30th and 40th passages of attenuated virus in kittens was determined.

Experiment 85-01—19th passage of 79-1146 in kittens: Table 3 lists the experimental design for experiment 85-01, the evaluation of passage 19 attenuated virus in 12- to 16-week-old kittens each. Group A served as unvaccinated controls, Group B received 0.5 ml (100,000 TCID$_{50}$) of vaccine virus intranasally, and Group C received the same dose of vaccine subcutaneously. Cats were observed and scored for clinical signs of illness as per a standard scoring procedure wherein each sign of clinical disease such as depression, liver, anorexia, pneumonia, nasal discharge, diarrahea were scored on a 0 to 4 basis 0=normal, 1=slight, 2=moderate, 3=marked, 4=severe). Daily group scores were totaled and a group mean clinical score for each day calculated. Rectal temperatures were recorded daily, pharyngeal swabs were taken 3 times per week for viral isolation, and weekly serum samples were obtained from the jugular vein for virus neutralizing antibody titer determination. Cats were to be challenged by aerosol with virulent FIPV-UCD$_1$ on day 21 after vaccination.

The individual and group mean temperatures of cats in this experiment are listed in Table 4 (Groups A, B, and C). The individual and group mean clinical scores are listed in Table 5. The viral isolation results from pharyngeal swabs are listed in Table 6, and the virus neutralizing titers are given in Table 7.

The control, nonvaccinated kittens (Group A) remained healthy throughout the experiment. Temperatures were normal, clinical signs of illness were not detected, no virus was recovered from pharyngeal swabs through day 27, and virus neutralizing antibody titers in serum against 79-1146 remained normal through day 28. Two of these controls were fed, cleaned, temperatured and sampled after the kittens in Groups B and C in order to monitor the effectiveness of the isolation.

Five of the 6 kittens vaccinated intranasally (Group B) with the passage 19 vaccine showed moderate to severe clinical signs typical of FIP. Signs first appeared on day 2 after vaccination, reached a peak on day 7 or 8, and subsided to normal by day 10 or 11. Signs redeveloped around day 16 and became very severe until the kitten either died or was euthanized between day 26 and day 31. One kitten (HF5) had a mild febrile response on days 2, 3, 4, and 14, and was slightly depressed on days 6 to 8. This kitten did not develop the secondary disease and has remained healthy through day 120.

Virus was isolated from pharyngeal swabs from all 6 kittens receiving intranasal vaccine (Table 6). Virus was present by 1 day after vaccination in all cats, 5 of 6 were still positive for virus on day 6, but only 2 of 6 kittens had virus on day 8. All kittens were negative by day 11 after vaccination.

Virus neutralizing antibody titers in sera were low at day 7, then increase in each weekly sample through day 21. Four of 6 cats had increased titers on day 28 compared to day 21. One cat had died of FIP prior to day 28, and a second cat had a decreased titer.

All 6 cats that received the 19th passage of attenuated 79-1146 virus subcutaneously developed moderate to severe clinical signs of FIP (Tables 4 and 5). Other than signs first appearing about one day after signs first appeared in the intranasal group, the progression of the disease was similar in the 2 groups of cats. All 6 of these kittens developed secondary disease and either died or were euthanized with FIP.

No virus was recovered from any of the pharyngeal swabs from kittens vaccinated subcutaneously throughout the duration of the experiment (Table 6). Virus neutralizing titers in sera were essentially identical to those in the intranasal group (Table 7).

Since most of the vaccinated kittens in this experiment eventually developed clinical FIP, there was no need to challenge the control kittens with virulent virus.

Experiment 85-02—Living 21st passage 79-1146: The control cats (Group A) from experiment 85-01 were utilized to screen the virulence of the 21st passage of virus (9 low temperature passages). 4 of these cats were divided into 2 groups of 2 cats each. One group served as unvaccinated controls, and the second group (Group D) received 1.0 ml of live 21st passage virus subcutaneously.

The 2 cats in group D(HD1 and HG4) received a single subcutaneous dose of vaccine containing $10^6$ $TCID_{50}$ of virus.

The clinical response of the 2 cats in Group D are listed in Tables 4 and 5. The response was similar to that observed in Groups B and C. Both cats developed primary disease, recovered, then develop secondary disease typical of FIP. One cat died and the other cat was euthanized on day 32.

The 2 controls were challenged on day 28 with virulent $UCD_1$ virus. Both cats developed clinical FIP. The temperatures of these cats after challenge are listed in Table 8.

The neutralizing titers of these cats after vaccination are listed in Table 9. The 2 control cats did not have neutralizing titers through day 21. The 2 cats receiving the 21st passage of live virus first had titers on day 14.

Experiment 85-03—30th passage of 79-1146 in kittens: Six SPF kittens 14 weeks of age were divided into 3 groups of 2 kittens each. Group E received 1.0 ml ($10^{7.5} TCID_{50}$) of the 30th passage of FIPV 79-1146 subcutaneously. Group F received the same volume and dose intranasally. Group G served as the nonvaccinated controls.

The clinical signs and temperature responses of these kittens after vaccination are listed in Tables 4 and 5. The response was substantially less dramatic than that for kittens exposed to passages 19 and 21. The primary disease was milder and of shorter duration in both of the vaccinated groups. Both of the kittens vaccinated subcutaneously (MG1, ME6, Group E) did develop secondary disease. ME6 was euthanized on day 21 with fluid in one lung and in the heart sac. Lesions of FIP were not detected in the peritoneum. Kitten MG1 was euthanized on day 31, and had fluid on one lung, pneumonia, and possible cardiomyopathy. Both cats were running fevers and were thin prior to euthanasia.

The 2 kittens that received the 30th passage of virus intranasally showed only mild primary disease, and little in the way of secondary disease. Kitten ME2 had a low grade febrile response on days 2, 3, 8, 18, 21, and 35, but did have a temperature of 105.2 on day 7. Kitten ME3 had low grade fever on days 2, 9, 23, 28, 30, 32, and 35. Since temperatures were not recorded on every day during the secondary disease phase, kittens in all likelihood had fever on more days than were recorded. As of the date of this report (day 54 after vaccination), both of these cats are still alive and reasonably healthy. They are thinner than the controls and are periodically showing low grade fevers, but they are bright, alert, and continue to eat.

Experiment 85-04—Comparison of 40th passage of FIPV-79-1146 attenuated live virus with the 6th passage of FIPV-Cornell-1: Fourteen 14-week-old Liberty Lab SPF kittens were divided into 4 groups of 2 kittens each as outlined in Table 10. Group A was the nonvaccinated control, Groups B and C received attenuated live virus intranasally and subcutaneously (1.0 ml/kitten of a 1:3,000 dilution of 40th passage of virus, or $10^4 TCID_{50}$/kitten).

Group G kittens received 1.0 ml ($10^4 TCID_{50}$) subcutaneously of the 6th passage of the Cornell-1 (CU-1) isolate of FIPV.

As of day 23 after vaccination both of the kittens vaccinated intranasally with the attenuated 40th passage of virus, plus the controls, have remained healthy and have not exhibited signs of primary disease. Fever has not been detected in these cats. This is in distinct contrast to the febrile response with the lower passages of virus. One of the 2 kittens vaccinated with 40th passage subcutaneously has not developed a fever, but the other kitten has had a fever on days 3, 7, and 8 after vaccination and was euthanized on day 23 with lesions of FIP.

The 2 kittens receiving the CU-1 virus subcutaneously both exhibited low grade fever on day 3. Otherwise they have been healthy through day 23.

Experiment 85-05—Recheck of the attenuation, efficacy, and sensitizing properties of the 18th passage of FIPV-1146 in adult cats: Four adult SPF cats, approximately 40 weeks of age, were vaccinated with the 18th passage of FIPV 79-1146. Two of these cats (W3, Z4) were Liberty Lab cats that had been uninoculated controls in a previous experiment and did not have antibodies to FIPV. The other 2 cats (73, 52) were control cats from another experiment, had come from a colony where most every kitten seroconverted to feline coronaviruses, and these seropositive cats were sensitized to challenge with FIPV-UCD$_1$.

All 4 cats developed antibody titers to 79-1146 ranging from slightly under 1:100 to 1:4,800. These cats were challenged via aerosol with UCD$_1$. They have remained healthy with no febrile response or other signs of illness for a period of 56 days (Table 7, Group Z). Neutralizing antibody titers rose slightly but not dramatically after challenge.

TABLE 3

Experimental Design, Experiment 85-01 - FIP Vaccine Study

| Group | Route of Vaccination | Cage # | Cat # | Sex | FIPV Challenge |
|---|---|---|---|---|---|
| A | None | 36 | J1 | F | UCD$_1$ |
|   |   |   | F4 | F |   |
|   |   | 40 | G4 | M |   |
|   |   |   | D1 | M |   |
|   |   | 23 | D2 | M |   |
|   |   |   | A6 | M |   |
| B | Intranasal | 21 | G2 | M | UCD$_1$ |
|   |   |   | F5 | M |   |
|   |   | 27 | F6 | M |   |
|   |   |   | A5 | M |   |
|   |   | 35 | C1 | F |   |
|   |   |   | B1 | F |   |
| C | Subcutaneous | 24 | A7 | M | UCD$_1$ |
|   |   |   | E4 | M |   |
|   |   | 25 | G3 | M |   |
|   |   |   | C2 | M |   |
|   |   | 26 | B2 | F |   |
|   |   |   | E3 | F |   |

Vaccine = FIPV-1146 Passage 19 ($10^{4.5}$ TCID$_{50}$/0.1 ml) Dilute 3.5 ml stock virus in 4.5 ml PBS. Each vaccinate received 0.5 ml or $10^{3.08}$ TCID$_{50}$
Challenge = Aerosol challenge on day 21 with liver suspension of virulent FIPV-UCD$_1$ virus.
VN antibody titers = weekly
Clinical disease evaluation = daily
Viral isolation from pharyngeal swabs = three times per week after vaccination
Temperature = Daily

TABLE 4

Temperature of Cats after "Vaccination" with attenuated Feline Infectious Peritonitis Virus Strain 79-1146

| Group | Vaccine Passage Level | Route | Dose (ml) | Cat # | Age (wks) | | Temperature (F. − 100) (Days After "Vaccination") 0 | 1 | 2 | 3 | 4 | 5 |
|---|---|---|---|---|---|---|---|---|---|---|---|---|
| A | Control | — | — | HJ1 | 15 | | 1.6 | 1.6 | 1.4 | 1.4 | 1.0 | 1.8 |
|   |   |   |   | HF4 | 15 | | 2.4 | 2.2 | 2.4 | 3.2 | 1.6 | 3.2 |
|   |   |   |   | HD1 | 15 | | 1.2 | 2.4 | 1.4 | 1.6 | 1.8 | 2.2 |
|   |   |   |   | HG4 | 15 | | 1.2 | 2.2 | 2.0 | 1.8 | 0.6 | 1.8 |
|   |   |   |   | HD2 | 15 | | 1.8 | 2.4 | 2.2 | 2.0 | 2.0 | 2.4 |
|   |   |   |   | HA6 | 15 | | 1.8 | 2.8 | 2.2 | 2.2 | 2.4 | 2.8 |
|   |   |   |   |   |   | Mean | 1.7 | 2.3 | 1.9 | 2.0 | 1.6 | 2.4 |
| B | P19 | SC | 0.5 | HA7 | 15 | | 2.0 | 2.0 | 2.6 | 3.6 | 3.6 | 3.0 |
|   |   |   |   | HE4 | 15 | | 0.8 | 2.6 | 2.8 | 2.8 | 2.2 | 2.4 |
|   |   |   |   | HG3 | 15 | | 2.2 | 2.0 | 2.2 | 3.6 | 3.0 | 3.8 |
|   |   |   |   | HC2 | 15 | | 2.6 | 2.4 | 2.0 | 4.0 | 3.8 | 2.8 |
|   |   |   |   | HB2 | 15 | | 2.0 | 1.4 | 2.2 | 3.6 | 4.2 | 2.8 |
|   |   |   |   | HE3 | 15 | | 2.0 | 2.2 | 1.8 | 3.8 | 3.4 | 2.6 |
|   |   |   |   |   |   | Mean | 1.9 | 2.1 | 2.3 | 3.6 | 3.4 | 2.9 |
| C | P19 | IN | 0.5 | HG2 | 15 | | 2.0 | 2.0 | 3.8 | 3.6 | 3.0 | 2.6 |
|   |   |   |   | HF5 | 15 | | 2.0 | 2.6 | 3.2 | 3.0 | 3.0 | 1.6 |
|   |   |   |   | HF6 | 15 | | 2.2 | 2.8 | 2.8 | 2.8 | 2.4 | 1.8 |
|   |   |   |   | HA5 | 15 | | 2.6 | 2.8 | 3.2 | 4.2 | 3.2 | 2.8 |
|   |   |   |   | HC1 | 15 | | 1.2 | 2.4 | 3.2 | 5.0 | 4.0 | 3.0 |
|   |   |   |   | HB1 | 15 | | 2.2 | 3.0 | 4.0 | 4.0 | 2.2 | 3.0 |
|   |   |   |   |   |   | Mean | 2.0 | 2.6 | 3.4 | 3.8 | 3.0 | 2.5 |
| D | P21 | SC | 1.0 | HD1 | 21 | | 1.4 | 2.8 | 2.8 | 3.6 | 4.8 | 3.6 |
|   |   |   |   | HG4 | 21 | | 1.6 | 1.2 | 2.0 | 2.2 | 4.2 | 3.6 |
|   |   |   |   |   |   | Mean | 1.5 | 2.0 | 2.4 | 2.9 | 4.5 | 3.6 |
| E | P30 | SC | 1.0 | MG1 | 14 | | 1.8 | 2.6 | 3.6 | 2.4 | 3.2 | 1.0 |
|   |   |   |   | ME6 | 14 | | 2.8 | 2.8 | 3.4 | 3.0 | 2.8 | 2.2 |
|   |   |   |   |   |   | Mean | 2.3 | 2.7 | 3.5 | 2.7 | 3.0 | 1.6 |
| F | P30 | IN | 1.0 | ME2 | 14 | | 2.4 | 3.8 | 3.2 | 2.8 | 1.8 | 2.2 |
|   |   |   |   | ME3 | 14 | | 2.4 | 2.6 | 3.6 | 2.6 | 2.8 | 2.2 |
|   |   |   |   |   |   | Mean | 2.4 | 3.2 | 3.4 | 2.7 | 2.3 | 2.2 |
| G | Control | — | — | MF5 | 14 | | 1.2 | 2.0 | 2.2 | 2.6 | 2.0 | 1.8 |
|   |   |   |   | MI5 | 14 | | 1.8 | 2.4 | 2.2 | 2.4 | 2.4 | 2.2 |
|   |   |   |   |   |   | Mean | 2.0 | 2.2 | 2.2 | 2.5 | 2.2 | 2.0 |

| Group | Vaccine Passage Level | Route | Dose (ml) | Cat # | Age (wks) | | Temperature (F. − 100) (Days After "Vaccination") 6 | 7 | 8 | 9 | 10 | 11 |
|---|---|---|---|---|---|---|---|---|---|---|---|---|
| A | Control | — | — | HJ1 | 15 | | 1.0 | 1.8 | 1.4 | 1.6 | 2.2 | 2.0 |
|   |   |   |   | HF4 | 15 | | 1.8 | 1.8 | 5.8 | 1.8 | 2.0 | 4.6 |
|   |   |   |   | HD1 | 15 | | 1.6 | 1.8 | 1.2 | 1.4 | 2.0 | 1.8 |
|   |   |   |   | HG4 | 15 | | 1.4 | 2.2 | 1.2 | 1.6 | 1.2 | 1.2 |
|   |   |   |   | HD2 | 15 | | 2.4 | 2.0 | 2.0 | 1.8 | 2.0 | 1.0 |
|   |   |   |   | HA6 | 15 | | 2.2 | 2.0 | 2.2 | 1.4 | 1.0 | 2.2 |

TABLE 4-continued

Temperature of Cats after "Vaccination" with attenuated
Feline Infectious Peritonitis Virus Strain 79-1146

|       |       |       |       |      |      |      | 1.7 | 1.9 | 2.3 | 1.6 | 1.7 | 2.2 |
|-------|-------|-------|-------|------|------|------|-----|-----|-----|-----|-----|-----|
| B     | P19   | SC    | 0.5   | HA7  | 15   |      | 4.0 | 3.6 | 3.2 | 4.4 | 3.0 | 4.0 |
|       |       |       |       | HE4  | 15   |      | 1.4 | 2.8 | 4.8 | 3.6 | 1.8 | 2.0 |
|       |       |       |       | HG3  | 15   |      | 4.8 | 3.6 | 4.0 | 2.4 | 2.4 | 4.2 |
|       |       |       |       | HC2  | 15   |      | 2.4 | 4.0 | 2.0 | 1.0 | 1.4 | 2.2 |
|       |       |       |       | HB2  | 15   |      | 2.0 | 2.2 | 2.0 | 1.6 | 1.4 | 1.8 |
|       |       |       |       | HE3  | 15   |      | 0.6 | 0.6 | 1.2 | 1.4 | 1.6 | 1.8 |
|       |       |       |       |      |      | Mean | 2.5 | 2.8 | 2.9 | 2.4 | 1.9 | 2.7 |
| C     | P19   | IN    | 0.5   | HG2  | 15   |      | 4.4 | 3.4 | 4.6 | 1.8 | 2.2 | 3.8 |
|       |       |       |       | HF5  | 15   |      | 1.4 | 2.2 | 1.8 | 2.0 | 1.8 | 1.8 |
|       |       |       |       | HF6  | 15   |      | 1.0 | 2.2 | 1.4 | 1.8 | 1.8 | 2.2 |
|       |       |       |       | HA5  | 15   |      | 5.2 | 3.8 | 3.2 | 1.8 | 2.4 | 4.4 |
|       |       |       |       | HC1  | 15   |      | 3.6 | 2.2 | 1.8 | 1.2 | 1.6 | 2.2 |
|       |       |       |       | HB1  | 15   |      | 3.6 | 3.8 | 2.8 | 1.6 | 1.8 | 1.0 |
|       |       |       |       |      |      | Mean | 3.2 | 2.9 | 2.6 | 1.7 | 1.9 | 2.6 |
| D     | P21   | SC    | 1.0   | HD1  | 21   |      | 3.2 | 2.8 | 4.0 | ND  | 2.0 | ND  |
|       |       |       |       | HG4  | 21   |      | 4.0 | 3.4 | 1.6 | ND  | 1.8 | ND  |
|       |       |       |       |      |      | Mean | 3.6 | 3.1 | 2.8 | ND  | 1.9 | ND  |
| E     | P30   | SC    | 1.0   | MG1  | 14   |      | 0.8 | 1.6 | 1.8 | 1.8 | 1.4 | 2.0 |
|       |       |       |       | ME6  | 14   |      | 1.6 | 3.4 | 1.4 | 2.2 | 1.0 | 1.4 |
|       |       |       |       |      |      | Mean | 1.2 | 2.5 | 1.6 | 2.0 | 1.2 | 1.7 |
| F     | P30   | IN    | 1.0   | ME2  | 14   |      | 5.2 | 3.8 | 1.8 | 2.2 | 2.2 | 2.2 |
|       |       |       |       | ME3  | 14   |      | 2.4 | 2.2 | 2.0 | 3.0 | 1.0 | 2.2 |
|       |       |       |       |      |      | Mean | 3.8 | 3.0 | 1.9 | 2.6 | 1.6 | 2.2 |
| G     | Control | —   | —     | MF5  | 14   |      | 2.2 | 1.0 | 2.0 | 2.4 | 1.8 | 1.8 |
|       |       |       |       | MI5  | 14   |      | 2.0 | 1.4 | 0.8 | 1.8 | 1.4 | 1.8 |
|       |       |       |       |      |      | Mean | 2.1 | 1.2 | 1.4 | 2.1 | 1.6 | 1.8 |

|       | Vaccine |       |       | Cats |      |      | Temperature (°F. − 100) |   |   |   |   |   |
|-------|---------|-------|-------|------|------|------|----|----|----|----|----|----|
|       | Passage |       | Dose  | Cat  | Age  |      | (Days After "Vaccination") | | | | | |
| Group | Level   | Route | (ml)  | #    | (wks)|      | 12 | 13 | 14 | 15 | 16 | 17 |
| A     | Control | —     | —     | HJ1  | 15   |      | 1.6 | 1.0 | 1.0 | 1.4 | 1.0 | 0.8 |
|       |         |       |       | HF4  | 15   |      | 1.6 | 2.4 | 2.0 | 3.0 | 2.0 | 2.2 |
|       |         |       |       | HD1  | 15   |      | 2.0 | 1.4 | 0.6 | 2.1 | 2.0 | 1.2 |
|       |         |       |       | HG4  | 15   |      | 1.2 | 1.2 | 1.4 | 1.7 | 1.5 | 0.8 |
|       |         |       |       | HD2  | 15   |      | 2.0 | 2.2 | 1.8 | 2.6 | 2.9 | 2.2 |
|       |         |       |       | HA6  | 15   |      | 2.2 | 2.2 | 1.8 | 2.6 | 2.7 | 2.0 |
|       |         |       |       |      |      | Mean | 1.8 | 1.7 | 1.4 | 2.2 | 2.0 | 1.5 |
| B     | P19     | SC    | 0.5   | HA7  | 15   |      | 2.0 | 5.4 | 5.8 | 4.4 | 6.0 | 5.0 |
|       |         |       |       | HE4  | 15   |      | 3.6 | 2.4 | 2.6 | 3.7 | 4.6 | 6.0 |
|       |         |       |       | HG3  | 15   |      | 5.4 | 5.2 | 6.0 | 3.5 | 4.4 | 4.6 |
|       |         |       |       | HC2  | 15   |      | 2.2 | 3.2 | 5.0 | 2.2 | 4.2 | 3.6 |
|       |         |       |       | HB2  | 15   |      | 2.2 | 1.6 | 1.2 | 2.0 | 1.1 | 2.2 |
|       |         |       |       | HE3  | 15   |      | 2.0 | 1.8 | 1.8 | 1.8 | 2.6 | 3.6 |
|       |         |       |       |      |      | Mean | 2.9 | 3.3 | 3.7 | 2.9 | 3.8 | 4.2 |
| C     | P19     | IN    | 0.5   | HG2  | 15   |      | 4.2 | 4.8 | 5.2 | 4.0 | 5.0 | 5.2 |
|       |         |       |       | HF5  | 15   |      | 2.0 | 1.8 | 3.2 | 2.3 | 2.2 | 2.6 |
|       |         |       |       | HF6  | 15   |      | 2.0 | 2.2 | 2.0 | 2.6 | 1.8 | 1.6 |
|       |         |       |       | HA5  | 15   |      | 4.4 | 5.2 | 5.0 | 2.0 | 5.0 | 5.0 |
|       |         |       |       | HC1  | 15   |      | 1.8 | 3.2 | 2.4 | 1.4 | 0.8 | 1.8 |
|       |         |       |       | HB1  | 15   |      | 1.8 | 2.2 | 3.4 | 4.3 | 5.1 | 5.2 |
|       |         |       |       |      |      | Mean | 2.7 | 3.2 | 3.5 | 2.8 | 3.3 | 3.7 |
| D     | P21     | SC    | 1.0   | HD1  | 21   |      | 3.6 | 3.6 | 3.6 | ND  | ND  | ND  |
|       |         |       |       | HG4  | 21   |      | 3.4 | 4.4 | 3.8 | ND  | ND  | ND  |
|       |         |       |       |      |      | Mean | 3.5 | 4.0 | 3.7 | ND  | ND  | ND  |
| E     | P30     | SC    | 1.0   | MG1  | 14   |      | ND  | 3.2 | ND  | 3.4 | 3.4 | ND  |
|       |         |       |       | ME6  | 14   |      | ND  | 2.2 | ND  | 2.8 | 3.0 | ND  |
|       |         |       |       |      |      | Mean | ND  | 2.7 | ND  | 3.1 | 3.2 | ND  |
| F     | P30     | IN    | 1.0   | ME2  | 14   |      | ND  | 2.6 | ND  | 2.2 | 3.0 | ND  |
|       |         |       |       | ME3  | 14   |      | ND  | 2.8 | ND  | 2.6 | 2.0 | ND  |
|       |         |       |       |      |      | Mean | ND  | 2.7 | ND  | 2.4 | 2.5 | ND  |
| G     | Control | —     | —     | MF5  | 14   |      | ND  | 2.0 | ND  | 1.8 | 2.2 | ND  |
|       |         |       |       | MI5  | 14   |      | ND  | 2.4 | ND  | 1.2 | 2.4 | ND  |
|       |         |       |       |      |      | Mean | ND  | 2.2 | ND  | 1.5 | 2.3 | ND  |

|       | Vaccine |       |       | Cats |      |      | Temperature (°F. ÷ 100) |   |   |   |   |   |
|-------|---------|-------|-------|------|------|------|----|----|----|----|----|----|
|       | Passage |       | Dose  | Cat  | Age  |      | (Days After "Vaccination") | | | | | |
| Group | Level   | Route | (ml)  | #    | (wks)|      | 18 | 19 | 20 | 21 | 22 | 23 |
| A     | Control |       |       | HJ1  | 15   |      | 1.4 | 1.0 | 1.0 | 0.6 | 1.2 | ND  |
|       |         |       |       | HF4  | 15   |      | 2.4 | 2.4 | 2.6 | 1.8 | 2.0 | ND  |
|       |         |       |       | HD1  | 15   |      | 2.2 | 1.8 | 1.8 | 1.2 | 1.4 | ND  |
|       |         |       |       | HG4  | 15   |      | 2.0 | 1.4 | 1.4 | 1.0 | 1.6 | ND  |
|       |         |       |       | HD2  | 15   |      | 1.8 | 2.4 | 2.2 | 2.2 | 2.4 | ND  |
|       |         |       |       | HA6  | 15   |      | 2.0 | 2.0 | 2.2 | 2.0 | 1.8 | ND  |
|       |         |       |       |      |      | Mean | 2.0 | 1.8 | 1.9 | 1.6 | 1.7 | ND  |

TABLE 4-continued

Temperature of Cats after "Vaccination" with attenuated
Feline Infectious Peritonitis Virus Strain 79-1146

| Group | Passage Level | Route | Dose (ml) | Cat # | Age (wks) | | | | | | |
|---|---|---|---|---|---|---|---|---|---|---|---|
| B | P19 | SC | 0.5 | HA7 | 15 | | 6.0 | 6.4 | 6.4 | 6.0 | 5.4 | ND |
| | | | | HE4 | 15 | | 5.6 | 5.4 | 5.2 | 5.4 | 5.0 | ND |
| | | | | HG3 | 15 | | 4.4 | 4.4 | 4.0 | 4.2 | 4.0 | ND |
| | | | | HC2 | 15 | | 4.4 | 3.4 | 3.4 | 2.8 | 2.2 | ND |
| | | | | HB2 | 15 | | 1.8 | 2.0 | 1.8 | 2.2 | 3.0 | ND |
| | | | | HE3 | 15 | | 4.2 | 4.6 | 4.8 | 4.2 | 4.0 | ND |
| | | | | | | Mean | 4.4 | 4.4 | 4.3 | 4.1 | 3.9 | ND |
| C | P19 | IN | 0.5 | HG2 | 15 | | 4.6 | 5.0 | 4.8 | 5.2 | 5.0 | ND |
| | | | | HF5 | 15 | | 3.0 | 3.2 | 2.6 | 2.2 | 2.4 | ND |
| | | | | HF6 | 15 | | 2.4 | 3.0 | 3.8 | 2.8 | 3.8 | ND |
| | | | | HA5 | 15 | | 5.8 | 5.4 | 5.2 | 5.2 | 5.0 | ND |
| | | | | HC1 | 15 | | 2.0 | 3.8 | 2.2 | 2.4 | 2.0 | ND |
| | | | | HB1 | 15 | | 6.0 | 5.4 | 5.0 | 4.6 | 4.6 | ND |
| | | | | | | Mean | 4.0 | 4.3 | 3.9 | 3.7 | 3.8 | ND |
| D | P21 | SC | 1.0 | HD1 | 21 | | 5.4 | ND | ND | 2.4 | ND | 1.8 |
| | | | | HG4 | 21 | | 5.2 | ND | ND | 2.4 | ND | 2.0 |
| | | | | | | Mean | 5.3 | ND | ND | 2.4 | ND | 1.9 |
| E | P30 | SC | 1.0 | MG1 | 14 | | 3.0 | ND | ND | 3.8 | ND | 4.2 |
| | | | | ME6 | 14 | | 4.2 | ND | ND | 3.2 | * | |
| | | | | | | Mean | 3.6 | ND | ND | 3.5 | ND | 4.2 |
| F | P30 | IN | 1.0 | ME2 | 14 | | 4.2 | ND | ND | 3.8 | ND | 2.6 |
| | | | | ME3 | 14 | | 2.4 | ND | ND | 2.8 | ND | 3.0 |
| | | | | | | Mean | 3.3 | ND | ND | 3.3 | ND | 2.8 |
| G | Control | — | — | MF5 | 14 | | 2.0 | ND | ND | ND | 4.6 | ND |
| | | | | MI5 | 14 | | 1.8 | ND | ND | ND | 4.8 | ND |
| | | | | | | Mean | 1.9 | ND | ND | ND | 4.7 | ND |

| | Vaccine | | | Cats | | Temperature (°F. − 100) | | | | |
|---|---|---|---|---|---|---|---|---|---|---|
| | Passage | | Dose | Cat | Age | (Days After "Vaccination") | | | | |
| Group | Level | Route | (ml) | # | (wks) | 24 | 25 | 26 | 27 | 28 |
| A | Control | — | — | HJ1 | 15 | ND | 2.0 | ND | 1.0 | ND |
| | | | | HF4 | 15 | ND | 1.8 | ND | 2.4 | ND |
| | | | | HD1 | 15 | ND | 2.2 | ND | 1.8 | ND |
| | | | | HG4 | 15 | ND | 2.0 | ND | 1.2 | ND |
| | | | | HD2 | 15 | ND | 2.0 | ND | 1.6 | ND |
| | | | | HA6 | 15 | ND | 1.6 | ND | 2.4 | ND |
| | | | | | Mean | ND | 1.9 | ND | 1.7 | ND |
| B | P19 | SC | 0.5 | HA7 | 15 | ND | * | | | |
| | | | | HE4 | 15 | ND | 5.6 | ND | 4.8 | ND |
| | | | | HG3 | 15 | ND | 4.6 | ND | 5.2 | ND |
| | | | | HC2 | 15 | ND | 3.2 | ND | 3.4 | ND |
| | | | | HB2 | 15 | ND | 2.4 | ND | 3.4 | ND |
| | | | | HE3 | 15 | ND | 0.2 | * | | |
| | | | | | Mean | ND | 3.2 | ND | 4.2 | ND |
| C | P19 | IN | 0.5 | HG2 | 15 | ND | 3.4 | ND | 0.4 | * |
| | | | | HF5 | 15 | ND | 2.6 | ND | 2.8 | ND |
| | | | | HF6 | 15 | ND | 5.0 | ND | 5.0 | ND |
| | | | | HA5 | 15 | ND | 3.8 | ND | 3.6 | ND |
| | | | | HC1 | 15 | ND | 1.8 | ND | 1.6 | ND |
| | | | | HB1 | 15 | ND | 4.0 | ND | 3.0 | ND |
| | | | | | Mean | ND | 3.4 | ND | 2.7 | ND |
| D | P21 | SC | 1.0 | HD1 | 21 | ND | ND | ND | ND | 2.0 |
| | | | | HG4 | 21 | ND | ND | ND | ND | 2.0 |
| | | | | | Mean | ND | ND | ND | ND | 2.0 |
| E | P30 | SC | 1.0 | MG1 | 14 | ND | ND | ND | ND | 4.8 |
| | | | | ME6 | 14 | | | | | |
| | | | | | Mean | ND | ND | ND | ND | 4.8 |
| F | P30 | IN | 1.0 | ME2 | 14 | ND | ND | ND | ND | 2.0 |
| | | | | ME3 | 14 | ND | ND | ND | ND | 3.8 |
| | | | | | Mean | ND | ND | ND | ND | 2.9 |
| G | Control | — | — | MF5 | 14 | ND | ND | ND | ND | 3.4 |
| | | | | MI5 | 14 | ND | ND | ND | ND | 2.6 |
| | | | | | Mean | ND | ND | ND | ND | 3.0 |

\* = Animal Died
ND = Not Determined

TABLE 5

Total Clinical Scores of cats after "Vaccination" with
Attenuated Feline Infectious Peritonitis Virus Strain
79-1146

| | Vaccine | | | Cats | | Clinical Scores | | | | | |
|---|---|---|---|---|---|---|---|---|---|---|---|
| | Passage | | Dose | Cat | Age | (Days After "Vaccination") | | | | | |
| Group | Level | Route | (ml) | # | (wks) | 0 | 1 | 2 | 3 | 4 | 5 |

TABLE 5-continued

Total Clinical Scores of cats after "Vaccination" with
Attenuated Feline Infectious Peritonitis Virus Strain
79-1146

| Group | Vaccine Passage Level | Route | Dose (ml) | Cat # | Age (wks) | | 0 | 1 | 2 | 3 | 4 | 5 |
|---|---|---|---|---|---|---|---|---|---|---|---|---|
| A | Control | — | — | HJ1 | 15 | | .0 | 0 | 0 | 0 | 0 | 0 |
|   |         |   |   | HF4 | 15 | | 0 | 0 | 0 | 1 | 0 | 1 |
|   |         |   |   | HD4 | 15 | | 0 | 0 | 0 | 0 | 0 | 0 |
|   |         |   |   | HG1 | 15 | | 0 | 0 | 0 | 0 | 0 | 0 |
|   |         |   |   | HD2 | 15 | | 0 | 0 | 0 | 0 | 0 | 0 |
|   |         |   |   | HA6 | 15 | | 0 | 0 | 0 | 0 | 0 | 0 |
|   |         |   |   |     |    | Mean | 0 | 0 | 0 | .2 | 0 | .2 |
| B | P19 | SC | 0.5 | HA7 | 15 | | 0 | 0 | 0 | 1 | 2 | 4 |
|   |     |    |     | HE4 | 15 | | 0 | 0 | 0 | 0 | 1 | 3 |
|   |     |    |     | HG3 | 15 | | 0 | 0 | 0 | 1 | 1 | 3 |
|   |     |    |     | HC2 | 15 | | 0 | 0 | 0 | 2 | 1 | 2 |
|   |     |    |     | HB2 | 15 | | 0 | 0 | 0 | 1 | 2 | 2 |
|   |     |    |     | HE3 | 15 | | 0 | 0 | 0 | 1 | 1 | 2 |
|   |     |    |     |     |    | Mean | 0 | 0 | 0 | 1.0 | 1.3 | 2.7 |
| C | P19 | IN | 0.5 | HG2 | 15 | | 0 | 0 | 1 | 1 | 1 | 0 |
|   |     |    |     | HF5 | 15 | | 0 | 0 | 1 | 1 | 1 | 0 |
|   |     |    |     | HF6 | 15 | | 0 | 0 | 0 | 0 | 0 | 0 |
|   |     |    |     | HA5 | 15 | | 0 | 0 | 1 | 2 | 1 | 0 |
|   |     |    |     | HC1 | 15 | | 0 | 0 | 1 | 3 | 2 | 1 |
|   |     |    |     | HB1 | 15 | | 0 | 1 | 2 | 2 | 0 | 1 |
|   |     |    |     |     |    | Mean | 0 | .2 | 1.0 | 1.5 | .8 | .3 |
| D | P21 | SC | 1.0 | HD1 | 21 | | 0 | 0 | 0 | 1 | 3 | 2 |
|   |     |    |     | HG4 | 21 | | 0 | 0 | 0 | 0 | 3 | 2 |
|   |     |    |     |     |    | Mean | 0 | 0 | 0 | .5 | 3 | 2 |
| E | P30 | SC | 1.0 | MG1 | 14 | | 0 | 0 | 1 | 0 | 1 | 0 |
|   |     |    |     | ME6 | 14 | | 0 | 0 | 1 | 1 | 0 | 0 |
|   |     |    |     |     |    | Mean | 0 | 0 | 1 | .5 | .5 | 0 |
| F | P30 | IN | 0.5 | ME2 | 14 | | 0 | 0 | 1 | 1 | 0 | 0 |
|   |     |    |     | ME3 | 14 | | 0 | 0 | 1 | 0 | 0 | 0 |
|   |     |    |     |     |    | Mean | 0 | 0 | 1 | .5 | 0 | 0 |
| G | Control | — | — | MF5 | 14 | | 0 | 0 | 0 | 0 | 0 | 0 |
|   |         |   |   | MI5 | 14 | | 0 | 0 | 0 | 0 | 0 | 0 |
|   |         |   |   |     |    | Mean | 0 | 0 | 0 | 0 | 0 | 0 |

| Group | Vaccine Passage Level | Route | Dose (ml) | Cat # | Age (wks) | | 6 | 7 | 8 | 9 | 10 | 11 |
|---|---|---|---|---|---|---|---|---|---|---|---|---|
| A | Control | — | — | HJ1 | 15 | | 0 | 0 | 0 | 0 | 0 | 0 |
|   |         |   |   | HF4 | 15 | | 0 | 0 | 3 | 0 | 0 | 2 |
|   |         |   |   | HD4 | 15 | | 0 | 0 | 0 | 0 | 0 | 0 |
|   |         |   |   | HG1 | 15 | | 0 | 0 | 0 | 0 | 0 | 0 |
|   |         |   |   | HD2 | 15 | | 0 | 0 | 0 | 0 | 0 | 0 |
|   |         |   |   | HA6 | 15 | | 0 | 0 | 0 | 0 | 0 | 0 |
|   |         |   |   |     |    | Mean | 0 | 0 | .5 | 0 | 0 | .3 |
| B | P19 | SC | 0.5 | HA7 | 15 | | 6 | 6 | 8 | 5 | 2 | 2 |
|   |     |    |     | HE4 | 15 | | 4 | 5 | 8 | 4 | 1 | 0 |
|   |     |    |     | HG3 | 15 | | 7 | 9 | 10 | 4 | 1 | 2 |
|   |     |    |     | HC2 | 15 | | 4 | 11 | 10 | 4 | 1 | 0 |
|   |     |    |     | HB2 | 15 | | 4 | 8 | 8 | 3 | 1 | 0 |
|   |     |    |     | HE3 | 15 | | 4 | 4 | 4 | 3 | 1 | 0 |
|   |     |    |     |     |    | Mean | 4.8 | 7.8 | 8.6 | 3.8 | 1.2 | .7 |
| C | P19 | IN | 0.5 | HG2 | 15 | | 5 | 10 | 9 | 3 | 1 | 1 |
|   |     |    |     | HF5 | 15 | | 1 | 2 | 2 | 0 | 0 | 0 |
|   |     |    |     | HF6 | 15 | | 1 | 2 | 2 | 0 | 0 | 0 |
|   |     |    |     | HA5 | 15 | | 4 | 7 | 6 | 1 | 0 | 2 |
|   |     |    |     | HC1 | 15 | | 4 | 4 | 3 | 2 | 0 | 0 |
|   |     |    |     | HB1 | 15 | | 4 | 5 | 3 | 2 | 0 | 0 |
|   |     |    |     |     |    | Mean | 3.2 | 5.0 | 4.2 | 1.3 | .2 | .5 |
| D | P21 | SC | 1.0 | HD1 | 21 | | 2 | 1 | 5 | ND | 0 | ND |
|   |     |    |     | HG4 | 21 | | 3 | 1 | 1 | ND | 0 | ND |
|   |     |    |     |     |    | Mean | 2.5 | 1 | 3 | ND | 0 | ND |
| E | P30 | SC | 1.0 | MG1 | 14 | | 0 | 0 | 0 | 0 | 0 | 0 |
|   |     |    |     | ME6 | 14 | | 0 | 4 | 1 | 0 | 0 | 0 |
|   |     |    |     |     |    | Mean | 0 | 2 | .5 | 0 | 0 | 0 |
| F | P30 | IN | 0.5 | ME2 | 14 | | 0 | 6 | 3 | 0 | 0 | 0 |
|   |     |    |     | ME3 | 14 | | 0 | 0 | 0 | 1 | 0 | 0 |
|   |     |    |     |     |    | Mean | 0 | 3 | 1.5 | .5 | 0 | 0 |
| G | Control | — | — | MF5 | 14 | | 0 | 0 | 0 | 0 | 0 | 0 |
|   |         |   |   | MI5 | 14 | | 0 | 0 | 0 | 0 | 0 | 0 |
|   |         |   |   |     |    | Mean | 0 | 0 | 0 | 0 | 0 | 0 |

| Group | Vaccine Passage Level | Route | Dose (ml) | Cat # | Age (wks) | | 12 | 13 | 14 | 15 | 16 | 17 |
|---|---|---|---|---|---|---|---|---|---|---|---|---|

TABLE 5-continued

Total Clinical Scores of cats after "Vaccination" with
Attenuated Feline Infectious Peritonitis Virus Strain
79-1146

| Group | Vaccine Passage Level | Route | Dose (ml) | Cat # | Age (wks) | | 12 | 13 | 14 | 15 | 16 | 17 |
|---|---|---|---|---|---|---|---|---|---|---|---|---|
| A | Control | — | — | HJ1 | 15 | | 0 | 0 | 0 | 0 | 0 | 0 |
| | | | | HF4 | 15 | | 0 | 0 | 0 | 1 | 0 | 0 |
| | | | | HD4 | 15 | | 0 | 0 | 0 | 0 | 0 | 0 |
| | | | | HG1 | 15 | | 0 | 0 | 0 | 0 | 0 | 0 |
| | | | | HD2 | 15 | | 0 | 0 | 0 | 0 | 0 | 0 |
| | | | | HA6 | 15 | | 0 | 0 | 0 | 0 | 0 | 0 |
| | | | | | | Mean | 0 | 0 | 0 | .2 | 0 | 0 |
| B | P19 | SC | 0.5 | HA7 | 15 | | 0 | 3 | 4 | 5 | 9 | 13 |
| | | | | HE4 | 15 | | 1 | 0 | 0 | 1 | 2 | 7 |
| | | | | HG3 | 15 | | 3 | 3 | 5 | 1 | 2 | 3 |
| | | | | HC2 | 15 | | 0 | 0 | 1 | 4 | 0 | 2 |
| | | | | HB2 | 15 | | 0 | 0 | 0 | 0 | 0 | 0 |
| | | | | HE3 | 15 | | 0 | 0 | 1 | 0 | 0 | 4 |
| | | | | | | Mean | .7 | 1.2 | 2.3 | 1.2 | 2.5 | 4.8 |
| C | P19 | IN | 0.5 | HG2 | 15 | | 2 | 2 | 4 | 3 | 4 | 5 |
| | | | | HF5 | 15 | | 0 | 0 | 1 | 0 | 0 | 0 |
| | | | | HF6 | 15 | | 0 | 0 | 0 | 0 | 0 | 0 |
| | | | | HA5 | 15 | | 2 | 3 | 4 | 0 | 3 | 5 |
| | | | | HC1 | 15 | | 0 | 1 | 0 | 0 | 0 | 0 |
| | | | | HB1 | 15 | | 0 | 0 | 1 | 2 | 3 | 5 |
| | | | | | | Mean | .7 | 1.0 | 1.7 | .8 | 1.7 | 2.5 |
| D | P21 | SC | 1.0 | HD1 | 21 | | 1 | 1 | 1 | ND | ND | ND |
| | | | | HG4 | 21 | | 1 | 2 | 1 | ND | ND | ND |
| | | | | | | Mean | 1 | 1.5 | ND | ND | ND | ND |
| E | P30 | SC | 1.0 | MG1 | 14 | | ND | 1 | ND | 1 | 1 | ND |
| | | | | ME6 | 14 | | ND | 0 | ND | 0 | 1 | ND |
| | | | | | | Mean | ND | .5 | ND | .5 | 1 | ND |
| F | P30 | IN | 0.5 | ME2 | 14 | | ND | 0 | ND | 0 | 0 | ND |
| | | | | ME3 | 14 | | ND | 0 | ND | 0 | 0 | ND |
| | | | | | | Mean | ND | 0 | ND | 0 | 0 | ND |
| G | Control | — | — | MF5 | 14 | | ND | 0 | ND | 0 | 0 | ND |
| | | | | MI5 | 14 | | ND | 0 | ND | 0 | 0 | ND |
| | | | | | | Mean | ND | 0 | ND | 0 | 0 | ND |

| Group | Vaccine Passage Level | Route | Dose (ml) | Cat # | Age (wks) | | 18 | 19 | 20 | 21 | 22 | 23 |
|---|---|---|---|---|---|---|---|---|---|---|---|---|
| A | Control | — | — | HJ1 | 15 | | 0 | 0 | 0 | 0 | 0 | ND |
| | | | | HF4 | 15 | | 0 | 0 | 0 | 0 | 0 | ND |
| | | | | HD4 | 15 | | 0 | 0 | 0 | 0 | 0 | ND |
| | | | | HG1 | 15 | | 0 | 0 | 0 | 0 | 0 | ND |
| | | | | HD2 | 15 | | 0 | 0 | 0 | 0 | 0 | ND |
| | | | | HA6 | 15 | | 0 | 0 | 0 | 0 | 0 | ND |
| | | | | | | Mean | 0 | 0 | 0 | 0 | 0 | ND |
| B | P19 | SC | 0.5 | HA7 | 15 | | 14 | 15 | 12 | 13 | 13 | ND |
| | | | | HE4 | 15 | | 5 | 7 | 7 | 8 | 10 | ND |
| | | | | HG3 | 15 | | 3 | 4 | 4 | 6 | 5 | ND |
| | | | | HC2 | 15 | | 2 | 3 | 3 | 3 | 3 | ND |
| | | | | HB2 | 15 | | 0 | 0 | 1 | 0 | 0 | ND |
| | | | | HE3 | 15 | | 6 | 7 | 7 | 9 | 9 | ND |
| | | | | | | Mean | 5.2 | 6.0 | 5.7 | 6.5 | 6.7 | ND |
| C | P19 | IN | 0.5 | HG2 | 15 | | 4 | 9 | 6 | 10 | 9 | ND |
| | | | | HF5 | 15 | | 1 | 1 | 0 | 0 | 0 | ND |
| | | | | HF6 | 15 | | 0 | 1 | 1 | 0 | 1 | ND |
| | | | | HA5 | 15 | | 5 | 12 | 12 | 12 | 12 | ND |
| | | | | HC1 | 15 | | 0 | 1 | 0 | 0 | 0 | ND |
| | | | | HB1 | 15 | | 6 | 6 | 6 | 6 | 8 | ND |
| | | | | | | Mean | 2.7 | 5.0 | 4.2 | 5.0 | 5.0 | ND |
| D | P21 | SC | 1.0 | HD1 | 21 | | 4 | ND | ND | 1 | 4 | 1 |
| | | | | HG4 | 21 | | 5 | ND | ND | 2 | 5 | 4 |
| | | | | | | Mean | 4.5 | ND | ND | 1.5 | 4.5 | 2.5 |
| E | P30 | SC | 1.0 | MG1 | 14 | | 1 | ND | ND | 1 | ND | 2 |
| | | | | ME6 | 14 | | 2 | ND | ND | * | | |
| | | | | | | Mean | 1.5 | ND | ND | | ND | 2 |
| F | P30 | IN | 0.5 | ME2 | 14 | | 1 | ND | ND | 6 | ND | 0 |
| | | | | ME3 | 14 | | 0 | ND | ND | 0 | ND | 1 |
| | | | | | | Mean | 1.5 | ND | ND | 3 | ND | .5 |
| G | Control | — | — | MF5 | 14 | | 0 | ND | ND | 0 | ND | 0 |
| | | | | MI5 | 14 | | 0 | ND | ND | 0 | ND | 0 |
| | | | | | | Mean | 0 | ND | ND | 0 | ND | 0 |

| Group | Vaccine Passage Level | Route | Dose (ml) | Cat # | Age (wks) | 24 | 25 | 26 | 27 | 28 |
|---|---|---|---|---|---|---|---|---|---|---|

TABLE 5-continued

Total Clinical Scores of cats after "Vaccination" with
Attenuated Feline Infectious Peritonitis Virus Strain
79-1146

| | | | | | | | | | | | |
|---|---|---|---|---|---|---|---|---|---|---|---|
| A | Control | — | — | HJ1 | 15 | | ND | 0 | ND | 0 | ND |
| | | | | HF4 | 15 | | ND | 0 | ND | 0 | ND |
| | | | | HD4 | 15 | | ND | 0 | ND | 0 | ND |
| | | | | HC1 | 15 | | ND | 0 | ND | 0 | ND |
| | | | | HD2 | 15 | | ND | 0 | ND | 0 | ND |
| | | | | HA6 | 15 | | ND | 0 | ND | 0 | ND |
| | | | | | | Mean | ND | 0 | ND | 0 | ND |
| B | P19 | SC | 0.5 | HA7 | 15 | | ND | * | | | |
| | | | | HE4 | 15 | | ND | 7 | ND | 4 | ND |
| | | | | HG3 | 15 | | ND | 4 | ND | 5 | ND |
| | | | | HC2 | 15 | | ND | 3 | ND | 4 | ND |
| | | | | HB2 | 15 | | ND | 0 | ND | 1 | ND |
| | | | | HE3 | 15 | | ND | 9 | * | | |
| | | | | | | Mean | ND | 4.6 | ND | 3.5 | ND |
| C | P19 | IN | 0.5 | HG2 | 15 | | ND | 10 | ND | 10 | * |
| | | | | HF5 | 15 | | ND | 1 | ND | 1 | ND |
| | | | | HF6 | 15 | | ND | 6 | ND | 5 | ND |
| | | | | HA5 | 15 | | ND | 4 | ND | 8 | ND |
| | | | | HC1 | 15 | | ND | 0 | ND | 0 | ND |
| | | | | HB1 | 15 | | ND | 10 | ND | 10 | ND |
| | | | | | | Mean | ND | 5.0 | ND | 5.7 | ND |
| D | P21 | SC | 1.0 | HD1 | 21 | | 1 | 3 | 4 | 5 | 9 |
| | | | | HG4 | 21 | | 6 | 7 | 8 | 10 | 11 |
| | | | | | | Mean | 3.5 | 5 | 6 | 7.5 | 10 |
| E | P30 | SC | 1.0 | MG1 | 14 | | ND | ND | ND | ND | 2 |
| | | | | ME6 | 14 | | | | ND | ND | |
| | | | | | | Mean | ND | ND | ND | ND | 2 |
| F | P30 | IN | 0.5 | ME2 | 14 | | ND | ND | ND | ND | 0 |
| | | | | ME3 | 14 | | ND | ND | ND | ND | 1 |
| | | | | | | Mean | ND | ND | ND | ND | .5 |
| G | Control | — | — | MF5 | 14 | | ND | ND | ND | ND | 0 |
| | | | | MI5 | 14 | | ND | ND | ND | ND | 0 |
| | | | | | | Mean | ND | ND | ND | ND | 0 |

*Animal Died
ND = Not Determined

TABLE 6

Virus Isolation from Pharyngeal Swab Samples from Cats
Vaccinated with the 19th Passage of FIPV 79-1146

| Group | Cat No. | Virus Isolation (Days Post Vaccination) | | | | | | | | | | | | | | | |
|---|---|---|---|---|---|---|---|---|---|---|---|---|---|---|---|---|---|
| | | 0 | | 1 | | 4 | | 6 | | 8 | | 11 | | 13 | 21 | 27 | |
| A | J1 | 0 | 0* | 0 | 0 | 0 | 0 | 0 | 0 | 0 | 0 | 0 | 0 | 0 | 0 | 0 | 0 |
| | F4 | 0 | 0 | 0 | 0 | 0 | 0 | 0 | 0 | 0 | 0 | 0 | 0 | 0 | 0 | 0 | 0 |
| | G4 | 0 | 0 | 0 | 0 | 0 | 0 | 0 | 0 | 0 | 0 | 0 | 0 | 0 | 0 | 0 | 0 |
| | D1 | 0 | 0 | 0 | 0 | 0 | 0 | 0 | 0 | 0 | 0 | 0 | 0 | 0 | 0 | 0 | 0 |
| | D2 | 0 | 0 | 0 | 0 | 0 | 0 | 0 | 0 | 0 | 0 | 0 | 0 | 0 | 0 | 0 | 0 |
| | A6 | 0 | 0 | 0 | 0 | 0 | 0 | 0 | 0 | 0 | 0 | 0 | 0 | 0 | 0 | 0 | 0 |
| B | G2 | 0 | 0 | + | | + | | + | | 0 | 0 | 0 | 0 | 0 | 0 | +? | 0 |
| | F5 | 0 | 0 | + | | + | | + | | + | | 0 | 0 | 0 | 0 | 0 | 0 |
| | F6 | 0 | 0 | + | | + | | + | | + | | 0 | 0 | 0 | 0 | 0 | 0 |
| | A5 | 0 | 0 | + | | + | | 0 | 0 | 0 | 0 | 0 | 0 | 0 | 0 | 0 | 0 |
| | C1 | 0 | 0 | + | | + | | + | | 0 | 0 | 0 | 0 | 0 | 0 | 0 | 0 |
| | B1 | 0 | 0 | + | | + | | + | | 0 | 0 | 0 | 0 | 0 | 0 | 0 | 0 |
| C | A7 | 0 | 0 | 0 | 0 | 0 | 0 | 0 | 0 | 0 | 0 | 0 | 0 | 0 | 0 | 0 | died |
| | E4 | 0 | 0 | 0 | 0 | 0 | 0 | 0 | 0 | 0 | 0 | 0 | 0 | 0 | 0 | 0 | 0 |
| | G3 | 0 | 0 | 0 | 0 | 0 | 0 | 0 | 0 | 0 | 0 | 0 | 0 | 0 | 0 | 0 | 0 |
| | C2 | 0 | 0 | 0 | 0 | 0 | 0 | 0 | 0 | 0 | 0 | 0 | 0 | 0 | 0 | 0 | 0 |
| | B2 | 0 | 0 | 0 | 0 | 0 | 0 | 0 | 0 | 0 | 0 | 0 | 0 | 0 | 0 | 0 | 0 |
| | E3 | 0 | 0 | 0 | 0 | 0 | 0 | 0 | 0 | 0 | 0 | 0 | 0 | 0 | 0 | 0 | died |

0 = no CPE
+ = CPE
Isolations done in A-72 cells
*Left column = Results of 1st cell culture passage
Right column = Results of 2nd cell culture passage
A = nonvaccinated controls
B = vaccinated intranasally
C = vaccinated subcutaneously

TABLE 7

Virus Neutralization Antibody Titers in Cats Vaccinated with the 19th Passage of FIPV-79-1146.

| Group | Cat No. | \multicolumn{5}{c}{Neutralizing Titer (Days Post Vaccination)} | | | | |
|---|---|---|---|---|---|---|
| | | 0 | 7 | 14 | 21 | 28 |
| A | J1 | 0 | 0 | 0 | 0 | 0 |
| | F4 | 0 | 0 | 0 | 0 | 0 |
| | G4 | 0 | 0 | 0 | 0 | 0 |
| | D1 | 0 | 0 | 0 | 0 | 0 |
| | D2 | 0 | 0 | 0 | 0 | 0 |
| | A6 | 0 | 0 | 0 | 0 | 0 |
| B | G2 | 0 | 6 | 96 | 384 | died |
| | F5 | 0 | 3 | 32 | 768 | 8192 |
| | F6 | 0 | 3 | 24 | 384 | 4096 |
| | A5 | 0 | 8 | 32 | 512 | 6144 |
| | C1 | 0 | 3 | 12 | 384 | 1534 |
| | B1 | 0 | 4 | 48 | 768 | 512 |
| C | A7 | 0 | <2 | 24 | 384 | died |
| | E4 | 0 | 4 | 16 | 192 | 2048 |
| | G3 | 0 | 4 | 32 | 768 | 8192 |
| | C2 | 0 | 2 | 48 | 512 | 2048 |
| | B2 | 0 | 2 | 32 | 256 | 4096 |
| | E3 | 0 | 3 | 24 | 96 | died |

Test done in A-72 Cells
$TCID_{50} = 48$

TABLE 9

Virus Antibody Titers in Kittens after Vaccination with Attenuated FIPV-79-1146

| Group | Cat No. | Neutralizing Titer (Days Post Vaccination) | | | |
|---|---|---|---|---|---|
| | | 0 | 7 | 14 | 21 |
| I | Control | | | | |
| | HD2 | <2 | <2 | <2 | <2 |
| | HD6 | <2 | <2 | <2 | <2 |
| | 1146-P21 | | | | |
| III | HD1 | <2 | <2 | 6 | 48 |
| | HG4 | <2 | <2 | 4 | 96 |

TABLE 10

Experimental Design of Experiment 85-04. Evaluation of attenuation of the 40th Passage of FIPV-79-1146, and the Virulence of the 6th Passage of FIPV-CU-1.

| Group | Route of Vaccination | Cage # | Cat # | Sex | FIPV Challenge |
|---|---|---|---|---|---|
| A Control | None | 31 | NT1 | M | UCD-1 |
| | | 31 | NR2 | M | UCD-1 |
| B 1146-P40 | Intranasal | 30 | NW6 | F | UCD-1 |
| | | 30 | NP4 | F | UCD-1 |
| C 1146-P40 | Subcutaneous | 29 | NX3 | F | UCD-1 |
| | | 29 | NY1 | F | UCD-1 |
| G | Subcutaneous | 21 | NR1 | F | UCD-1 |

TABLE 8

Temperature of Cats Vaccinated with Attenuated FIPV 79-1146 and Challenged* with FIPV-UCD-1

| Group | Vaccine Passage Level | Route | Dose (ml) | Cat # | Age (wks) | Temperature (°F. − 100) (Days After Challenge) | | | | | |
|---|---|---|---|---|---|---|---|---|---|---|---|
| | | | | | | 0 | 1 | 3 | 4 | 6 | 7 |
| Z | P18 | SC | 1.0 | W3 | 48 | 1.0 | ND | 1.6 | 1.0 | 1.6 | 1.4 |
| | | | | Z4 | 48 | 1.6 | ND | 0.8 | 0.6 | 2.8 | 2.8 |
| | | | | 73 | 48 | 2.0 | ND | 1.0 | 1.2 | 1.6 | 1.2 |
| | | | | 52 | 48 | 1.8 | \multicolumn{5}{c}{Too mean to temp.} | | | | |
| | | | | Mean | | 1.6 | ND | 1.1 | 0.9 | 2.0 | 1.8 |
| I | Control | — | — | HA6 | 25 | 1.6 | ND | 3.6 | 3.0 | 3.0 | 1.8 |
| | | | | HD2 | 25 | 1.8 | 2.0 | ND | 2.4 | 1.8 | 1.4 |
| | | | | Mean | | 1.7 | 1.8 | ND | 3.0 | 2.4 | 1.6 |

| Group | Vaccine Passage Level | Route | Dose (ml) | Cat # | Age (wks) | Temperature (°F. − 100) (Days After Challenge) | | | | | |
|---|---|---|---|---|---|---|---|---|---|---|---|
| | | | | | | 8 | 9 | 11 | 12 | 13 | 14 |
| Z | P18 | SC | 1.0 | W3 | 48 | ND | ND | 1.6 | ND | 1.8 | ND |
| | | | | Z4 | 48 | ND | ND | 2.0 | ND | 2.0 | ND |
| | | | | 73 | 48 | ND | ND | 1.0 | ND | 2.4 | ND |
| | | | | 52 | 48 | | | | | | |
| | | | | Mean | | ND | ND | 1.5 | ND | 2.1 | ND |
| I | Control | — | — | HA6 | 25 | 2.0 | 1.6 | ND | 3.0 | 3.6 | 3.6 |
| | | | | HD2 | 25 | 3.0 | 3.2 | ND | 3.8 | 4.4 | 4.0 |
| | | | | Mean | | 2.5 | 2.4 | ND | 3.4 | 4.0 | 3.8 |

| Group | Vaccine Passage Level | Route | Dose (ml) | Cat # | Age (wks) | Temperature (°F. + 100) (Days After Challenge) | | | |
|---|---|---|---|---|---|---|---|---|---|
| | | | | | | 15 | 20 | 25 | 28 |
| Z | P18 | SC | 1.0 | W3 | 48 | ND | 1.8 | ND | 2.0 |
| | | | | Z4 | 48 | ND | 2.0 | ND | 2.4 |
| | | | | 73 | 48 | ND | 2.8 | ND | 2.0 |
| | | | | 52 | 48 | | | | |
| | | | | Mean | | ND | 2.2 | ND | 2.1 |
| I | Control | — | — | HA6 | 25 | 4.0 | 4.6 | **+ | NA |
| | | | | HD2 | 25 | 4.4 | 3.4− | NA | NA |
| | | | | Mean | | 4.2 | 4.0 | NA | NA |

*Aerosol challenge of 0.5 to 1.0 ml/cat of a 1:50 dilution of liver homogenate.
**T98.0
ND = Not Determined
NA = Not Applicable
− = cat died or was euthanized with FIP TABLE 10-continued Experimental Design of Experiment 85-04. Evaluation of attenuation of the 40th Passage of FIPV-79-1146, and the Virulence of the 6th Passage of FIPV-CU-1.

| Group | Route of Vaccination | Cage # | Cat # | Sex | FIPV Challenge |
|---|---|---|---|---|---|
| CU1-P6 | | 21 | NV4 | F | UCD-1 |

14-week-old Liberty Kittens
Vaccine = FIPV 1146-P40 Dilute 1:3000 in PBS 1 ml per cat
Titer = $10^{7.5}TCID_{50}/0.1$ ml
Revaccinate Groups D, E, and F at 14 DPV
Challenge = Aerosol challenge with 50% liver suspension of FIPV-UDC-1
Antibody Titers = weekly
Clinical Disease evaluation = Daily
Temperature - Daily
Retitrate stock after exp.
Vaccine = Cu-1-P6 1 ml/cat
Titer = $10^{3.0}TCID_{50}/0.1$ ml
Retitrate after Exp.

The starting plaque purified 11th passage) virus WSU FIPV 79-1146 (also referred to as FIPV 79-1146 or 791146) has been deposited with the ATCC and has been assigned access No. VR 2125.

The 19th passage virus has been deposited with the ATCC and has been assigned accession No. VR 2126.

The 40th passage virus has been deposited with the ATCC and has been assigned accession No. VR 2127.

The 50th passage virus has been deposited with the ATCC and has been assigned accession No. VR 2128.

EXAMPLE 3

The above attenuated viruses (e.g. 40 or 50 passages) were able to protect adult cats by injecting sublethal doses of FIPV strain 1146 intratracheally followed by vaccination intranasally with the attenuated virus. This attenuated virus was, however, lethal for weaned SPF kittens vaccinated intranasally or subcutaneously.

The attenuation of this virus, FIPV-1146 was continued by further passage (as in Example 2) through cell cultures to a total of 100 cell culture pasages. The virus was tested at approximately every 10th passage in 12-week-old SPF kittens for safety and efficacy. Kittens were vaccinated by either the subcutaneous or intranasal routes, then monitored daily for evidence of adverse reactions including fever, inappetence, depression, and any other signs of illness. Weekly serum samples were assayed for neutralizing antibody titers against FIPV-1146. Five to seven weeks after vaccination, the immunity of these kittens was challenged by aerosol exposure to the 8th or 9th cell culture passage of virulent FIPV-1146. Again kittens were monitored for several weeks for evidence of fever and other clinical signs of illness as well as neutralizing antibody titers in their serums.

As the cell culture passage levels increased, the virulence of the virus decreased. There was a decided drop in the virulence for the intranasal route after the 30th passage, and for the subcutaneous route after the 60th passage. However, even in the 70—73rd passage level, while outward clinical signs of FIP were not produced after subcutaneous vaccination most cats did have a febrile response for one to several days, and many of these cats had elevated liver enzyme levels and elevated bilirubin levels 7 to 14 days after vaccination. While these cats developed high virus neutralizing titers after subcutaneous vaccination with the 73rd passage virus, only 40% of these kittens were protected against virulent virus challenge. As the passage of virus was continued beyond the 73rd passage, protection afforded by the subcutaneous route of vaccination diminished. A passage level of virus that was completely safe for subcutaneous vaccination while providing acceptable protection against virulent virus was not determined.

When the vaccine virus was given to SPF kittens by the intranasal route, there was attenuation of the virus at lower passage levels of virus compared to the subcutaneous route. However, some kittens still developed a febrile response through at least the 70th passage of virus. When young adult cats (6 to 8 months of age) were given intranasal vaccine virus in the 80 to 100th passage range, no adverse reactions to vaccination occurred, and excellent neutralizing antibody titers were produced. All 12 of these vaccinated cats had solid protection against intranasal FIPV challenge, with no fever or other signs of illness, while all 3 of the nonvaccinated controls developed fever and clinical FIP after challenge.

Cats vaccinated by the intranasal route, or challenged by aerosol exposure, shed virus in oropharyngeal secretions from approximately day 1 through day 9 after vaccination or exposure. After day 10, virus could not be recovered in swab samples from the pharynx of cats, even from those cats that were exhibiting signs of clinical FIP. Cats vaccinated by the subcutaneous route did not shed virus after vaccination. After challenge, nonvaccinated control cats shed virus, but vaccinated cats did not shed virus.

It appears that an effective and safe vaccine for FIP has be developed. When cats were vaccinated by the intranasal route, the degree of reaction to the vaccine was less, and the degree of protection against 1146 virulent virus challenge was greater. With the 80th to 100th passages of virus, 12 of 12 young adult vaccinated cats were protected against virulent virus challenge when the vaccine was given by the intranasal route.

The presently contemplated best mode is the use of the 100 passage attenuated virus vaccine given intranasally in two doses about 3 weeks apart.

The 80th passage virus has been deposited with the ATCC and has been assigned accession No. VR 2201.

The 100th passage virus has been deposited with the ATCC and has been assigned accession No. VR 2202.

We claim:

1. A method of protecting felines from infection caused by feline infectious peritonitis virus (FIPV) comprising inoculating an animal with modified living feline coronavirus vaccine prepared by serially passaging FIPV 79-1146 in non-oncogenic cell culture, in which virus growth occurs, at a temperature which causes virus growth and attenuation until a non-virulent, immunizing virus is produced.

2. The method of claim 1 wherein the serial passaging comprises at least about 40 passages.

3. The method of claim 2 wherein the serial passaging comprises at least about 80 passages.

4. The method as in claim 1 wherein the passage temperature is at a temperature lower than the normal body temperature for a feline.

5. The method as in claim 4 wherein the passage temperature is approximately 34° C.

6. The method as in claim 1 wherein the non-oncogenic cell culture is selected from the group consisting of FCWF and CrFK.

7. The method as in claim 1 wherein the FIPV 79-1146 strain is ATCC VR 2125.

8. A modified live vaccine for protecting felines against feline infectious peritonitis virus (FIPV) caused infection prepared by serially passaging FIPV 79-1146 in nononcogenic cell culture in which virus growth occurs at a temperature which causes virus growth and attenuation until a non-virulent, immunizing virus is produced.

9. The virus of claim 8 wherein the serial passaging comprises at least about 40 passages.

10. The virus of claim 8 wherein the serial passaging comprises at least about 80 passages.

11. The virus as in claim 8 wherein the passage temperature is at a temperature lower than the normal body temperature for a feline.

12. The virus as in claim 11 wherein the passage temperature is approximately 34° C.

13. The virus as in claim 8 wherein the non-oncogenic cell culture is selected from the group consisting of FCWF and CrFK.

14. The virus as in claim 8 wherein the FIPV 79-1146 strain is ATCC VR 2125.

15. The method of producing a modified live vaccine for protecting felines against feline infectious peritonitis virus (FIPV) caused infection which comprises:

(a) serially passaging FIPV 79-1146 in non-oncogenic cell culture at a temperature which causes virus growth and attenuation (b) periodically testing the passaged virus until a non-virulent immunizing virus is obtained.

16. The method of claim 15 wherein the serial passaging comprises at least about 40 passages.

17. The method of claim 15 wherein the serial passaging comprises at least about 80 passages.

18. The method as in claim 15 wherein the passage temperature is at a temperature lower than the normal body temperature for a feline.

19. The method as in claim 18 wherein the passage temperature is approximately 34° C.

20. The method as in claim 15 wherein the non-oncogenic cell culture is selected from the group consisting of FCUF and CrFK.

21. The method as in claim 15 wherein the FIPV 79-1146 strain is ATCC VR 2125.

22. The method of claim 1 where the animal is inoculated intranasally.

23. The method of claim 1 where the animal is inoculated intranasally with vaccine wherein the FIPV 79-1146 has been passaged at least about 80 passages.

* * * * *